(12) United States Patent
Ito et al.

(10) Patent No.: US 6,942,793 B2
(45) Date of Patent: Sep. 13, 2005

(54) LIQUID CHROMATOGRAPH MASS SPECTROMETER

(75) Inventors: Shinya Ito, Hitachinaka (JP); Kisaburo Deguchi, Sapporo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 23 days.

(21) Appl. No.: 10/778,047

(22) Filed: Feb. 17, 2004

(65) Prior Publication Data

US 2004/0173509 A1 Sep. 9, 2004

(30) Foreign Application Priority Data

Mar. 6, 2003 (JP) ........................................ 2003-059985

(51) Int. Cl.[7] .............................................. B01D 15/08
(52) U.S. Cl. .................... 210/198.2; 210/656; 210/659; 210/143
(58) Field of Search ................................ 210/635, 656, 210/659, 143, 198.2; 422/70; 436/161

(56) References Cited

U.S. PATENT DOCUMENTS

| | | | | |
|---|---|---|---|---|
| 5,135,718 A | * | 8/1992 | Kawaguchi et al. ........... | 422/70 |
| 5,958,227 A | * | 9/1999 | Uematsu .................. | 210/198.2 |
| 6,235,197 B1 | * | 5/2001 | Anderson et al. ........... | 210/635 |
| 6,344,172 B1 | | 2/2002 | Afeyan et al. | |
| 6,485,642 B2 | * | 11/2002 | Kaito et al. ............... | 210/198.2 |
| 6,498,040 B1 | * | 12/2002 | Yokoyama et al. .......... | 436/161 |
| 6,586,727 B2 | | 7/2003 | Bateman et al. | |
| 6,780,325 B1 | * | 8/2004 | Murata et al. ............... | 210/656 |
| 6,802,967 B2 | * | 10/2004 | Masuda et al. ........... | 210/198.2 |
| 2002/0011437 A1 | * | 1/2002 | Kaito et al. ............... | 210/198.2 |
| 2002/0146349 A1 | * | 10/2002 | Gygi et al. .................... | 422/70 |
| 2003/0168392 A1 | * | 9/2003 | Masuda et al. ........... | 210/198.2 |

* cited by examiner

Primary Examiner—Ernest G. Therkorn
(74) Attorney, Agent, or Firm—Dickstein Shapiro Morin & Oshinsky LLP (57) ABSTRACT

A liquid chromatograph mass spectrometer comprises: a pump; a sample injector; a plurality of separation columns, including a first separation column and a second separation column; and mass spectrometer. The liquid chromatograph mass spectrometer further comprises: a plurality of trap columns for retaining a sample component separated by the first separation column; a first switching valve for switching between one of the plurality of trap columns and another one of the plurality of trap columns at regular time intervals in such a way that when the one of the plurality of trap columns is connected to the first separation column, the another one of the plurality of trap columns is connected to the pump, and vice versa; and a second switching valve for, when a trap column is connected to the pump, further connecting the trap column to the second separation column after connecting the trap column to solution discharging means during a predetermined initial time period, the second separation column being connected to the mass spectrometer and capable of separating the sample component in a shorter time than the first separation column.

3 Claims, 6 Drawing Sheets

LIQUID CHROMATOGRAPH MASS SPECTROMETER

BACKGROUND OF THE INVENTION

The present invention relates to a liquid chromatograph mass spectrometer, and more particularly to a multidimensional liquid chromatograph mass spectrometer having a plurality of separation columns.

Liquid chromatograph mass spectrometers have been used to analyze sample solutions containing a plurality of components.

A liquid chromatograph mass spectrometer comprises: a liquid chromatograph which passes a sample through its separation column and thereby separates the components of the sample from one another by utilizing the fact that each component varies in its interaction with the column; and a mass spectrometer which ionizes the separated components one after another and detects the generated ions.

For analysis of a sample containing many species of components, a multidimensional liquid chromatograph mass spectrometer is used which includes a multidimensional liquid chromatograph having therein a plurality of separation columns connected in series to further separate the components from one another.

Examples of multidimensional liquid chromatograph mass spectrometers are described in Japanese Patent Laid-Open No. 3-175355 and Analytical Chemistry, 69 (1997), pp. 1518–1524.

Japanese Patent Laid-Open No. 62-255865 describes a liquid chromatograph which does not employ series-connected separation columns but in which a sample concentration column, a reaction column, and a separation column are connected in series.

The technique described in Japanese Patent Laid-Open No. 62-255865 supplies an eluent to a separation column while supplying a sample solution to a concentration column to concentrate it. When the concentration and the separation have been completed, the flow path switching valve is switched so as to supply a solution for desorption to the separation column through the concentration column and a reaction column.

The technique described in Japanese Patent Laid-Open No. 62-255865 allows the concentration and the separation to be carried out separately from each other, making it possible to select an optimum concentration method and optimum separation conditions.

Multidimensional liquid chromatograph mass spectrometers employ a plurality of columns using different separation principles.

The reason for this is that the first and second columns require different types of eluent for separation.

That is, when a cation exchange column is used as the first separation column, for example, an electrolyte solution having an appropriate concentration is used as the eluent. Electrolyte solution is not suitable as a solution introduced into a mass spectrometer.

Specifically, introducing an electrolyte solution into a mass spectrometer adversely affects it, such as reducing the ionization efficiency (and hence the detection sensitivity) and contaminating or clogging the ion sampling olifice. Therefore, electrolyte solution cannot be introduced into mass spectrometers.

This problem may be circumvented by using the technique described in Japanese Patent Laid-Open No. 62-255865, as follows. An electrolyte solution is supplied to the first separation column to separate a sample, which is then trapped in an appropriate trap column. After that, the flow path switching valve is switched so that the solution excluding the electrolyte solution, which can be introduced into the mass spectrometer, is supplied from the trap column to the second separation column so as to supply the separated sample to the mass spectrometer.

In this case, however, while the solution is being supplied from the trap column to the second separation column, that is, while the sample solution is being separated in the second separation column, the sample separation operation of the first column must be stopped. This means that the sample cannot be continuously supplied, and therefore the analysis takes a long time to complete.

Furthermore, in multidimensional liquid chromatograph mass spectrometers using a conventional technique, each of the plurality of separation columns takes a certain time to complete each separation operation. Therefore, the first column must stop its current separation operation until the second column connected in series to the first column completes its separation operation, making it impossible to continuously supply eluent from the first column to the second column.

Accordingly, in multidimensional liquid chromatograph mass spectrometers using a conventional technique, a fraction of eluted components including a target component(s) must be taken from the components eluted from the first separation column and introduced into the second column.

This means that even though these specific (selected) components can be measured, not all components contained in the sample solution can be measured.

To analyze all components contained in a sample solution, it is necessary to put the eluent from the first separation column into a plurality of sample loops or trap columns in fractions and sequentially introduce each fraction of eluent into the second separation column.

In this case, the time required for the second separation column to complete an entire separation operation is longer than when the eluent is not processed in fractions, since the time increases with the number of samples (fractions) taken from the eluent from the first separation column.

That is, the time it takes the entire analysis to complete is considerably long, as compared with ordinary liquid chromatograph mass spectrometers.

A biological sample must be analyzed in a short time. Therefore, the above method in which the eluent from the first separation column is processed in fractions cannot be used for biological samples.

Analysis requiring a long time to complete is not desirable even for samples other than biological samples.

SUMMARY OF THE INVENTION

The present invention relates to multidimensional liquid chromatograph mass spectrometers having a plurality of separation columns therein. An object of the present invention is to provide a liquid chromatograph mass spectrometer capable of performing quick detection without reducing the separation performance of each separation column and the detection sensitivity of the mass spectrometer.

To accomplish the above object, one aspect of the present invention provides a liquid chromatograph mass spectrometer comprising: a pump; a sample injector; a plurality of separation columns, including a first separation column and a second separation column; and mass spectrometer;

wherein the liquid chromatograph mass spectrometer further comprises: a plurality of trap columns for retaining a sample component separated by the first separation column; a first switching valve for switching between one of the plurality of trap columns and another one of the plurality of trap columns at regular time intervals in such a way that when the one of the plurality of trap columns is connected to the first separation column, the another one of the plurality of trap columns is connected to the pump, and vice versa; and a second switching valve for, when a trap column is connected to the pump, further connecting the trap column to the second separation column after connecting the trap column to solution discharging means during a predetermined initial time period, the second separation column being connected with the mass spectrometer and capable of separating the sample component in a shorter time than the first separation column.

According to another aspect of the present invention, the above liquid chromatograph mass spectrometer further comprises: a detector for detecting a chromatograph of a sample, the detector being disposed between the first separation column and the plurality of trap columns.

According to still another aspect of the present invention, in the above liquid chromatograph mass spectrometer, the second separation column is a monolithic column capable of performing separation at high speed.

According to yet another aspect of the present invention, there is provided a liquid chromatograph mass spectrometer comprising: a pump; a sample injector; a plurality of separation columns, including a first separation column and a plurality of second separation columns; and mass spectrometer; wherein the plurality of second separation columns further separate a sample component separated by the first separation column, the plurality of second separation columns being capable of separating the sample component in a shorter time than the first separation column; and wherein the liquid chromatograph mass spectrometer further comprises: a first switching valve for switching between one of the plurality of second separation columns and another one of the plurality of second separation columns at regular time intervals in such a way that when the one of the plurality of second separation columns is connected to the first separation column, the another one of the plurality of second separation columns is connected to the pump, and vice versa; and a second switching valve for, when a second separation column is connected to the pump, further connecting the second separation column to the mass spectrometer after connecting the second separation column to solution discharging means during a predetermined initial time period.

BRIEF DESCRIPTION OF THE DRAWINGS

Other objects and advantages of the invention will become apparent from the following description of embodiments with reference to the accompanying drawings in which:

FIG. 2 includes FIGS. 2A and 2B which are diagrams showing how a 10-port switching valve switches flow paths according to the first embodiment of the present invention;

FIG. 3 includes FIGS. 3A to 3C which are graphs showing chromatograms and a mass spectrum obtained using the first embodiment of the present invention;

FIG. 4 includes FIGS. 4A and 4B which are graphs for comparing chromatograms obtained using an ODS column and a monolithic column;

FIG. 6 includes FIGS. 6A and 6B which are diagrams showing how a 10-port switching valve switches flow paths according to the second embodiment of the present invention.

DETAILED DESCRIPTION OF THE PREFERRED EMBODIMENTS

Preferred embodiments of the present invention will be described below with reference to the accompanying drawings.

First Embodiment

Figure 1:
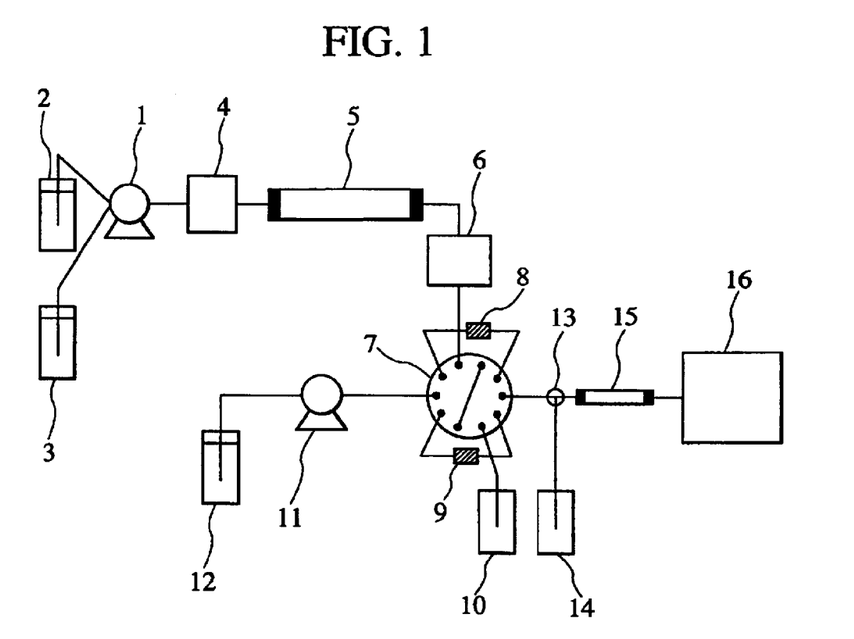
FIG. 1 is a schematic diagram showing the configuration of a liquid chromatograph mass spectrometer according to a first embodiment of the present invention.

FIG. 1 is a schematic diagram showing the configuration of a liquid chromatograph mass spectrometer according to a first embodiment of the present invention.

Referring to FIG. 1, a pump 1 supplies eluents 2 and 3 to a sample injector 4 at a constant flow rate while changing their composition ratio. The sample injector 4 injects a sample into the flow path together with the eluents supplied from the pump 1.

The components contained in the injected sample are fed to a separation column 5 and eluted in the order of increasing interaction with the separation column 5. Each component eluted from the separation column 5 is detected by an ultraviolet-visible absorbance detector 6 and then introduced to a 10-port switching valve 7.

The 10-port switching valve 7 is connected with two trap columns 8 and 9, and switches the flow paths such that the components eluted from the separation column 5 are supplied to the trap column 8 and the trap column 9 alternately at regular time intervals.

Figure 2A:
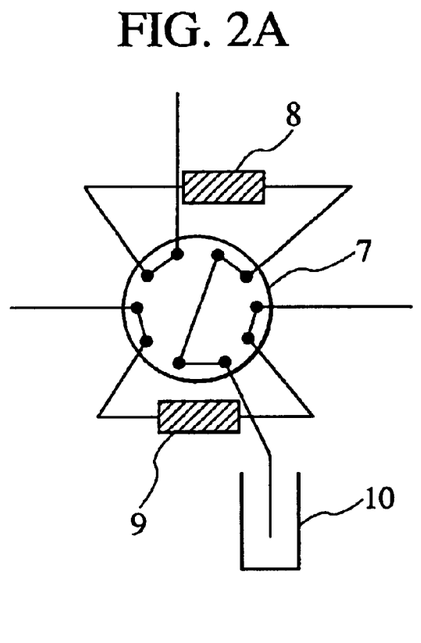
Figure 2B:
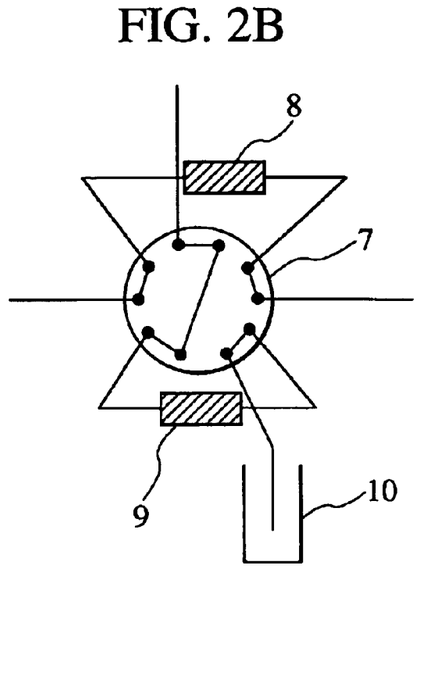

FIG. 2 (including FIGS. 2A and 2B) shows the flow paths formed by the 10-port switching valve 7.

The 10-port switching valve 7 can switch between two flow path formations, as shown in FIGS. 2A and 2B.

When the flow paths shown in FIG. 2A are formed by the 10-port valve 7, a sample is continuously supplied to the separation column 5 together with eluents, and the components which have passed through the separation column 5 and the ultraviolet-visible absorbance detector 6 are held in the trap column 8. A considerable portion of each eluent, which is not held in the trap column 8, is discharged from the trap column 8 to a waste solution bottle 10.

It should be noted that the trap column 9 is currently connected between a pump 11 and a switching valve 13 shown in FIG. 1 through flow paths.

A predetermined time after switching to the connection state shown in FIG. 2A, the 10-port switching valve 7 switches back to the connection state shown in FIG. 2B so that the trap column 8 is connected between the pump 11 and the switching valve 13 through flow paths. Then, the components and the eluents held in the trap column 8 are eluted by an eluent 12 introduced by the pump 11 at a constant flow rate.

Specifically, when the eluent 12 is supplied to the trap column 8, first the eluents 2 and 3 present within the trap column 8 are eluted from the trap column 8.

Since it is not desirable to supply the eluents 2 and 3 eluted from the trap column 8 to a mass spectrometer 16, they are discharged into a waste solution bottle 14 by way of the flow path switching valve 13.

After the eluents 2 and 3 have been eluted from the trap column 8 and before the components held in the trap column 8 are eluted, the flow path switching valve 13 is switched from the waste solution bottle 14 to a high-speed separation column 15 so that the components eluted from the trap column 8 are fed to the high-speed separation column 15.

In the state shown in FIG. 2B, the trap column 9 is connected to the separation column 5 through the ultraviolet-visible absorbance detector 6 and further connected to the path for discharging waste solution into the waste solution bottle 10. From the state shown in FIG. 2A to the state shown in FIG. 2B, the sample continues to be supplied to the separation column 5 without interruption. The sample is fed to the trap column 9 through the ultraviolet-visible absorbance detector 6. The components of the sample are held in the trap column 9, while a considerable portion of each eluent is discharged into the waste solution bottle 14.

The components which have been fed from the trap column 8 to the high-speed separation column 15 are further separated and eluted in the order of increasing interaction with the high-speed separation column 15. The eluted components are introduced to the mass spectrometer 16, which provides information on their mass numbers.

Since the high-speed separation column 15 takes less time to complete component separation than the separation column 5, the high-speed separation column 15 completes the component separation in a time shorter than the component trapping time of each of the trap columns 8 and 9.

A predetermined time after switching to the connection state shown in FIG. 2B, the 10-port switching valve 7 switches back to the connection state shown in FIG. 2A.

Thus, the 10-port switching value 7 switches between the connection state shown in FIG. 2A and that shown in FIG. 2B at regular time intervals.

It should be noted that the operations of the pumps 1 and 11, the 10-port switching valve 7, and the flow path switching valve 13 are controlled by the operation control unit (not shown).

Figure 3A:
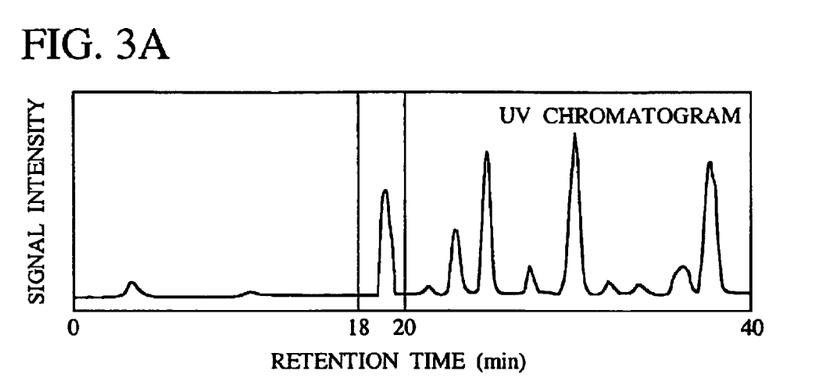
Figure 3B:
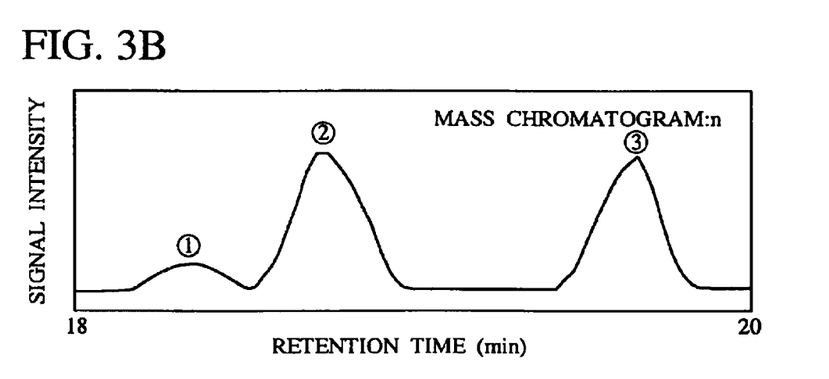
Figure 3C:
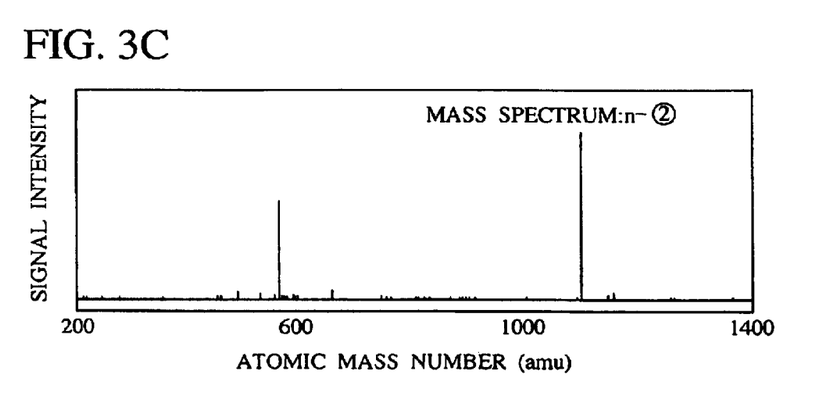

FIG. 3 (including FIGS. 3A to 3B) shows analysis results obtained when a measurement was made on a sample peptide compound using a cation exchange column and a monolithic column as the separation column 5 and the high-speed separation column 15, respectively, in the first embodiment shown in FIG. 1.

It should be noted that monolithic columns use cylindrical rods as their packing material, instead of spherical particles which have used by conventional columns, and therefore can perform component separation in a short time, as compared with conventional columns filled with spherical particles.

Figure 4A:
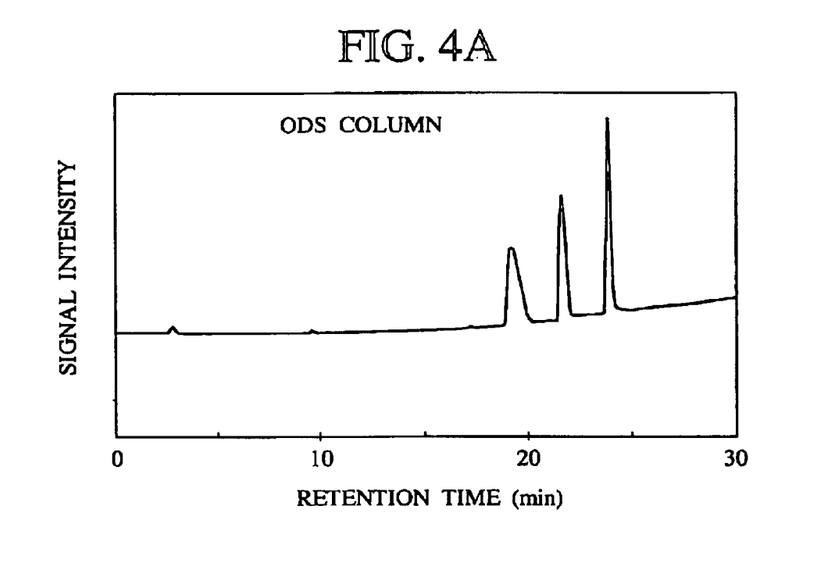
Figure 4B:
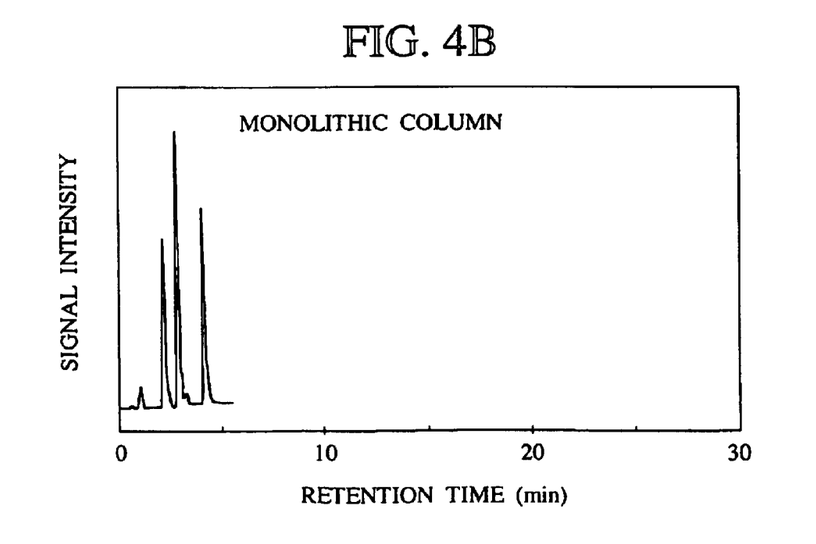

FIG. 4 (including FIGS. 4A and 4B) shows chromatograms obtained when the same components are analyzed using an ODS column containing spherical particles and a monolithic column using a cylindrical rod of silica as its carrier.

Specifically, FIG. 4A shows the chromatogram obtained using the ODS column, while FIG. 4B shows that obtained using the monolithic column. The ODS column took approximately 25 minutes to separate all components whereas the monolithic column took only 5 minutes or less.

FIG. 3A shows a UV chromatogram obtained by the ultraviolet-visible absorbance detector 6. The UV chromatogram shows the peak of each peptide component separated by the cation exchange column.

FIG. 3B shows a total ion chromatogram of components, obtained by the mass spectrometer 16. The components were eluted during the 2 minute time period between the two time points corresponding to the retention time 18 minutes and the retention time 20 minutes. The components were then fed to the trap column 8 and separated in the monolithic column 15 before they were mass analyzed.

In the UV chromatogram shown in FIG. 3A, the components are detected as a single peak in the 2 minute time period between the two time points corresponding to the retention times 18 minutes and 20 minutes. In the total ion chromatogram shown in FIG. 3B, on the other hand, they are detected as three component peaks ①, ②, and ③ separated by the monolithic column.

This is attributed to the fact that the cation exchange column and the monolithic column employ different separation mechanisms; the monolithic column can separate components which cannot be fully separated by the cation exchange column.

Further, since the monolithic column was used as the high-speed separation column 15, all the components were separated in only 2 minutes.

FIG. 3C shows a mass spectrum of the peak ② detected in the total ion chromatogram shown in FIG. 3B.

The cation exchange column uses the eluents 2 and 3 as buffer solutions to separate components. However, introducing the buffer solutions into the mass spectrometer 16 as they are decreases the component detection sensitivity.

To overcome this problem, the first embodiment of the present invention uses the trap columns 8 and 9 to wash away the eluents 2 and 3 (buffer solutions) with the eluent 12 containing no buffer solution, preventing the buffer solutions from entering the mass spectrometer 16.

This allows the mass spectrometer 16 to detect each component with high sensitivity. Analysis results according to the first embodiment of the present invention showed that to complete an analysis, a multidimensional liquid chromatograph mass spectrometer of the first embodiment took the same analysis time as do ordinary liquid chromatograph mass spectrometers using only a single separation column; that is, the multidimensional liquid chromatograph mass spectrometer can perform analysis in a very short time, as compared with conventional multidimensional liquid chromatograph mass spectrometers.

Further, since the monolithic column 15 capable of performing separation at high speed is used as the second separation column, the second separation column (monolithic column 15) can complete the component separation in a time shorter than the time required for the separation by the separation column 5, that is, the time required for the trap column to trap the components, making it possible to continuously supply the sample to the first separation column 5.

If the time taken by the second separation column to separate components is approximately equal to that taken by the first separation column to separate components, the separation completion time of the second separation column is delayed by the time required to discharge the buffer solutions retained within the trap column 8 or 9. This means that the sample supply to the first separation column must be halted during that time, making it impossible to continuously supply the sample to the first separation column 5.

As described above, the first embodiment of the present invention can provide a liquid chromatograph mass spectrometer capable of quickly detecting components without adversely affecting the separation performance of each of the plurality of separation columns and the detection sensitivity of the mass spectrometer.

An experiment conducted by the present inventor showed that a multidimensional liquid chromatogram mass spectrometer using a conventional technique took approximately 10 hours to complete an analysis whereas the first embodiment of the present invention took only approximately 30 minutes to 1 hour.

It should be noted that a high-speed separation column, represented by the monolithic column, is a separation column capable of separating components in a shorter time than the first separation column.

Second Embodiment

Figure 5:
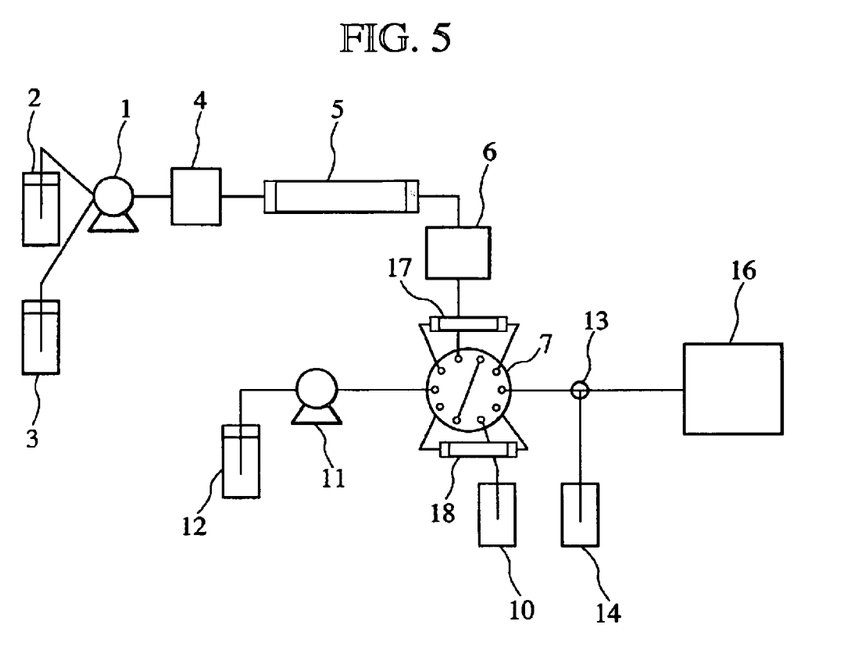
FIG. 5 is a schematic diagram showing the configuration of a liquid chromatograph mass spectrometer according to a second embodiment of the present invention.

FIG. 5 is a schematic diagram showing the configuration of a liquid chromatograph mass spectrometer according to a second embodiment of the present invention. The second embodiment is different from the first embodiment in that the second embodiment employs high-speed separation columns 17 and 18 instead of the trap columns 8 and 9 and has omitted the separation column 15. The other components are same as those of the first embodiment.

Figure 6A:
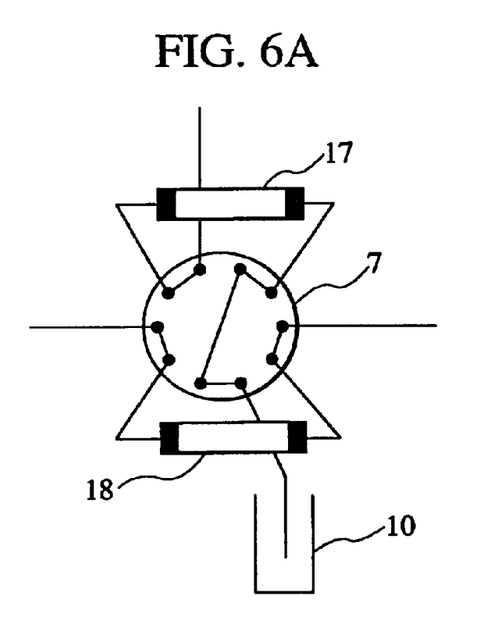
Figure 6B:
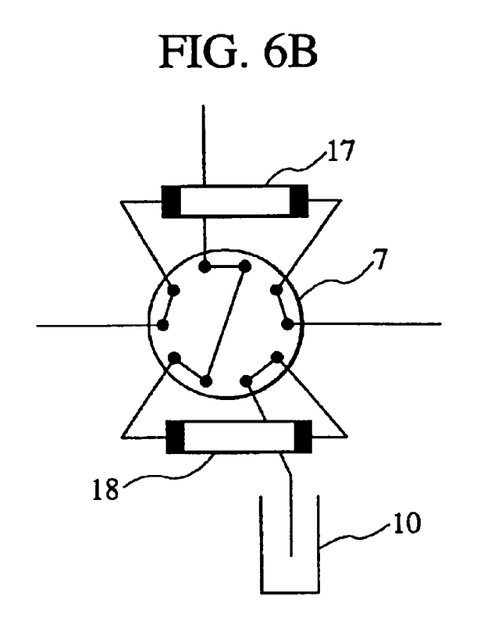

Referring to FIG. 5, the 10-port switching valve 7 switches the flow paths at regular time intervals so as to feed each component to either the high-speed separation column 17 or 18. FIG. 6 (including FIGS. 6A and 6B) shows the flow paths formed by the 10-port switching valve 7.

The 10-port switching valve 7 can switch between two flow path formations, as shown in FIGS. 6A and 6B. When the flow paths shown in FIG. 6A are formed by the 10-port switching valve 7, the components which have passed through the ultraviolet-visible absorbance detector 6 are held in the high-speed separation column 17. A considerable portion of each eluent, which is not held in the high-speed separation column 17, is eluted from the high-speed separation column 17 and discharged into the waste solution bottle 10.

After a predetermined time has elapsed, the 10-port switching valve 7 switches to the state shown in FIG. 6B.

In this state, the eluents 2 and 3 present within the high-speed separation column 17 are eluted from the high-speed separation column 17 by the action of the eluent 12 and discharged into the waste solution bottle 14 by way of the flow path switching valve 13.

After that, the switching valve 13 is switched from the waste solution bottle 14 to the mass spectrometer 16 side, so that each component held in the high-speed separation column 17 is separated and eluted in the order of increasing interaction with the high-speed separation column 17 by the action of the eluent 12 supplied by the pump 11 at a constant flow rate. Each component is then introduced into the mass spectrometer 16, which provides information on its mass number.

The components fed from the ultraviolet-visible absorbance detector 6 during that time are held in the high-speed separation column 18, and a considerable portion of each eluent is discharged into the waste solution bottle 14.

The second embodiment of the present invention can produce the same effect as that of the first embodiment.

The present invention provides multidimensional liquid chromatograph mass spectrometers having a plurality of separation columns. The present invention can provide a liquid chromatograph mass spectrometer capable of quickly detecting components without adversely affecting the separation performance of each separation column and the detection sensitivity of the mass spectrometer.

While the invention has been described in its preferred embodiments, it is to be understood that the words which have been used are words of description rather than limitation and that changes within the purview of the appended claims may be made without departing from the true scope and spirit of the invention in its broader aspects.

What is claimed is:

1. A liquid chromatograph mass spectrometer comprising:

a pump;

a sample injector;

a plurality of separation columns, including a first separation column and a second separation column; and mass spectrometer;

wherein said liquid chromatograph mass spectrometer further comprises:

a plurality of trap columns for retaining a sample component separated by said first separation column;

a first switching valve for switching between one of said plurality of trap columns and another one of said plurality of trap columns at regular time intervals in such a way that when said one of said plurality of trap columns is connected to said first separation column, said another one of said plurality of trap columns is connected to said pump, and vice versa; and a second switching valve for, when a trap column is connected to said pump, further connecting said trap column to said second separation column after connecting said trap column to solution discharging means during a predetermined initial time period, said second separation column being connected to said mass spectrometer and capable of separating said sample component in a shorter time than said first separation column.

2. The liquid chromatograph mass spectrometer as claimed in claim 1, further comprising:

a detector for detecting a chromatogram of a sample, said detector being disposed between said first separation column and said plurality of trap columns.

3. The liquid chromatograph mass spectrometer as claimed in claim 1, wherein said second separation column is a monolithic column capable of performing separation at high speed.

* * * * *